United States Patent [19]

Nyéki et al.

[11] Patent Number: 5,093,320

[45] Date of Patent: Mar. 3, 1992

[54] NOVEL PEPTIDES INHIBITING THE MATURATION OF T-LYMPHOCYTES AND THE ACTIVITY OF MACROPHAGES, PHARMACEUTICAL COMPOSITIONS CONTAINING THEM AND PROCESS FOR PREPARING SAME

[75] Inventors: Kuprina O. Nyéki; István Schon; Lajos Kisfaludy, deceased, late of Budapest, by Maria Kisfaludy, Marta Kisfaludy, András Kisfaludy, legal heirs; László Dénes, Budapest; György Hajós, Budapest; László Szporny, Budapest, all of Hungary

[73] Assignee: Richter Gedeon Vegyeszeti Gyar R. T., Budapest, Hungary

[21] Appl. No.: 462,219

[22] Filed: Jan. 9, 1990

[30] Foreign Application Priority Data

Jan. 13, 1989 [HU] Hungary ................. 116/89

[51] Int. Cl.$^5$ .................. C07K 5/08; C07K 5/10; A61K 37/02
[52] U.S. Cl. ..................... 514/18; 530/330; 530/331
[58] Field of Search ........... 514/16, 17; 530/329, 530/330, 331

[56] References Cited

U.S. PATENT DOCUMENTS

| | | | |
|---|---|---|---|
| 4,190,646 | 2/1980 | Goldstein et al. | 514/17 |
| 4,215,112 | 7/1980 | Goldstein et al. | 514/18 |
| 4,395,404 | 7/1983 | Low et al. | 514/18 |
| 4,428,938 | 1/1984 | Kisfaludy et al. | 514/17 |
| 4,442,031 | 4/1984 | Felix et al. | 530/329 |

FOREIGN PATENT DOCUMENTS

| | | |
|---|---|---|
| 0018182 | 10/1980 | European Pat. Off. . |
| 0033384 | 8/1981 | European Pat. Off. . |
| 0378432 | 7/1990 | European Pat. Off. . |

OTHER PUBLICATIONS

Drugs Exptl Clin Res XIII(6) 327–337 (1987), Talmadge J. E. et al.,
Drugs of the Future, 11, pp. 784–793 (1986).
U.S. patent application Ser. No. 07/123,124 (allowed) filed 20 Nov. 1977, which is equivalent to Hungarian Patent 4,827,186.

*Primary Examiner*—Lester L. Lee
*Assistant Examiner*—S. G. Marshall
*Attorney, Agent, or Firm*—Herbert Dubno; Jonathan Myers

[57] ABSTRACT

Peptides are disclosed which inhibit the immune system. The peptides are selected from the group consisting of:

Arg-Lys(Chc)-Asp-Val

Arg-Lys(Chc)-Asp

Arg-Sar-Asp-Val

Arg-Sar-Asp

Orn-Lys-Asp-Val

Orn-Lys-Asp

Arg-Lys-Aad-Val

Arg-Lys-Aad

[Arg-Lys-Asp-NH-CH$_2$-]$_2$

Arg—Lys—Asp—Val—NH—CH$_2$
                              |
Arg—Lys—Asp—NH—CH$_2$

[Arg—Lys—Asp—Val—NH—CH$_2$—]$_2$

[Arg—Lys—Asp—Cys—NH$_2$]$_2$

Lys-Ser-Lys-Leu

Ser-Lys-Leu

Ser-Ser-Ser-Thr

Lys-Glu-Thr

Lys-Thr-Glu-Thr

Pro-Lys-Leu-Thr

Lys-Lys-Thr-Glu and

Lys-His-Leu-NH$_2$, and pharmaceutically acceptable acid addition salts thereof.

4 Claims, No Drawings

NOVEL PEPTIDES INHIBITING THE MATURATION OF T-LYMPHOCYTES AND THE ACTIVITY OF MACROPHAGES, PHARMACEUTICAL COMPOSITIONS CONTAINING THEM AND PROCESS FOR PREPARING SAME

This invention relates to novel peptides of formulae (1) to (20)

| | |
|---|---|
| Arg-Lys(Chc)-Asp-Val | (1) |
| Arg-Lys(Chc)-Asp | (2) |
| Arg-Sar-Asp-Val | (3) |
| Arg-Sar-Asp | (4) |
| Orn-Lys-Asp-Val | (5) |
| Orn-Lys-Asp | (6) |
| Arg-Lys-Aad-Val | (7) |
| Arg-Lys-Aad | (8) |
| [Arg-Lys-Asp-NH-CH$_2$-]$_2$ | (9) |
| Arg—Lys—Asp—Val—NH—CH$_2$<br>\|<br>Arg—Lys—Asp—NH—CH$_2$ | (10) |
| [Arg—Lys—Asp—Val—NH—CH$_2$—]$_2$ | (11) |
| [Arg—Lys—Asp—Cys—NH$_2$]$_2$ | (12) |
| Lys-Ser-Lys-Leu | (13) |
| Ser-Lys-Leu | (14) |
| Ser-Ser-Ser-Thr | (15) |
| Lys-Glu-Thr | (16) |
| Lys-Thr-Glu-Thr | (17) |
| Pro-Lys-Leu-Thr | (18) |
| Lys-Lys-Thr-Glu | (19) |
| Lys-His-Leu-NH$_2$ | (20) | their acid addition salts and pharmaceutical compositions containing these peptides.

According to an other aspect of the invention, there is provided a process for the preparation of the novel peptides of formulae (1) to (20) and pharmaceutical compositions containing them.

The peptides of the above formulae (1) to (20) are capable to inhibiting the maturation of T-lymphocytes and the activity of macrophages.

The invention further relates to a method of treating (living) animals (including human) to influence the function of the immune system of the treated person or animal by administering (an) effective dose(s) of one or more compound(s) of the above formulae (1) to (20) per se or in the form of a pharmaceutical composition.

In a healthy organism the balanced function of the immune system maintains a strong protective mechanism which is capable of killing microorganisms, destroying foreign materials and tumor cells as well as removing them from the organism while the healthy cells of the organism itself are not damaged.

When the functioning of the immune system is decreased (suboptimal), the infective foreign or tumor cells can propagate which finally leads to the total destruction of functioning of the host organism; whereas, when the immune response is over-increased, healthy tissues may also be damaged (autoimmune and allergic diseases). In the course of e.g. organ transplantations, the organ or tissue implanted may be rejected by a natural defensive reaction (response) of the organism.

The thymus-originating lymphocytes, the so-called T-cells play a key role in starting, maintaining and suspending the immune response. It is known that, due to the information-transmission, the function of the immune system in the living organism is influenced by a number of peptides and proteins. Thymus hormones and information-transmitting factors (cytokins) produced by the immune cells have widely been investigated in treating tumor and immune diseases [Drugs of the Future 11, 784 (1986); Drugs Exp. Clin. Res. 13, 327 (1987)]. Such a factor is e.g. the so-called thymosine fraction 5, a partially-purified extract from calf thymus containing the known thymus hormones [Cancer Immunol. Immunther. 18, 185 (1984)]. Advantageous results have been obtained by using cytokins prepared by genetic engineering techniques for the treatment of cancer diseases [N. Engl. J. Med. 313, 1485 (1985)].

For pharmaceutical compositions, more and more severe quality demands are set up. When organ extracts and biosynthetic macromolecules are not pure enough to be homogenous, the contaminations (impurities) can cause undesired side effects. For this reason, efforts are made everywhere to use compositions with a precisely defined structure and high purity in therapy. An immunostimulating action mentioned above in connection with the macromolecules could be reached also by using smaller peptides (U.S. Pat. Nos. 4,190,646, 4,215,112, 4,232,008, 4,261,886, 4,395,404 and 4,442,031; German patent specifications Nos. 2,938,420, 3,001,775 and 3,100,974; Hungarian patent specification No. 185,263; and Hungarian patent application No. 4827/86).

The short peptides described in the references cited above initiate the proliferation of the T- and B-cells and possess a general immunostimulating effect. For reproducing the whole spectrum of action of the native immunomodulating agents, substances are required which exert their effect in various periods of the general immune response in a manner different from the known immunostimulating agents.

The peptides of the present invention exert a suppressing effect on the function of the immune system and, particularly, they inhibit the maturation of T-cells and activity of the macrophages. This action makes possible using these peptides for treating symptoms related to the increased function of the immune system. The immunosuppressing drugs currently used in therapy such as cyclophosphamide, i.e. 2-[-bis(2-chloroethyl)amino]-tetrahydro-2H-1,3,2-oxazaphosphorine-2-oxide; azathioprin, i.e. 6-(1-methyl-4-nitro-5-imidazolylthio)purine; corticosteriods or cyclosporin, possess a therapeutic index below 10, i.e. the therapeutic dose does not significantly differ from the toxic one, thus, they can be used only under a strict medical control.

A particular advantage of the immunosuppressive peptides is that they decompose very fast in the organism, do not accumulate in the tissues and cells; however, in spite of their short life-time, they are capable of initiating composite processes leading to a significant action. They are characterized by a low toxicity [$LD_{50} > 1000$ mg/kg intravenously (i.v.)].

It has been found that the novel peptides of the formulae (1) to (20) inhibit the maturation of the T-cell-dependent antibody-producing cells, decrease the activity of antibody-producing cells in newborn mice, suppress the phagocytosis and diminish the late hypersensitive response. The inhibitory effects of these peptides are based presumably on the phenomena that they suppress the antigen-presentation of macrophages and/or the antigen recognition of T-cells in the immune processes. Actually, the composite mechanism of the immune response is initiated by these processes and interactions; thus, it can be supposed that the immunosuppressive action of these peptides are effective in the beginning period of the immune response.

The novel peptides of formulae (1) to (20) of the invention are prepared by stepwise chain-lengthening in solution by successively employing coupling steps of an active ester, a mixed anhydride and/or an azide method, as are known in the peptide chemistry, followed by the deprotection of the α- and/or E-amino group(s), whereby starting with amino acid derivatives containing a carboxy group esterified by a protective group being removable by hydrogenation or acidolysis, and optionally a protected side-chain hydroxyl and/or amino group and/or a C-terminal carboxy group aminated or esterified by a protecting group being removable by hydrogenation, or starting with 1,2-diaminoethane, mono-L-valine derivative thereof or L-cystine diamide, derivatives of the peptides of formulae (1) to (20) are formed which are aminated or esterified on their C-terminal carboxy group by a protecting group being removable by hydrogenation or acidolysis, esterified on their other carboxyl by a protecting group being removable by hydrogenation or acidolysis, containing protective groups Boc or Z on their amino groups not involved in the peptide linkage and/or being protected on their hydroxyl group;

then removing the protecting groups present by catalytic hydrogenation and/or acidic treatment; and if desired, converting the free peptides of formulae (1) to (20) to their acid addition salts by treatment with a suitable acid; and/or, if desired, liberating the free peptides of formulae (1) to (20) obtained in the form of their salts and/or transforming to salts formed with another acid.

In some cases, a combination of protecting groups is used in the synthesis such as to make it possible to remove selectively the amino-protecting groups and then to cleave all protecting groups in one or two step(s) at the end of the synthesis. In order to form the peptide linkage, a method utilizing the N-hydroxysuccinimide esters [Wünsch: Synthese von Peptiden, Vol. 2, Georg Thieme Verlag, Stuttgart, 1974, page 14)], the pentafluorophenyl esters (Hungarian patent specification No. 168,431), or the mixed anhydrides (Hungarian patent specification No. 183,579) can be used.

For the synthesis of the dimer type compounds of formulae (9) to (12), 1,2-diaminoethane or its mono-L-valine derivative or L-cystine diamide are used as starting substances. In the stepwise chain-lengthening, about 2 moles of the acylating amino acid derivative, calculated for one mole of the above starting substance, are employed (the actual molar ratio depends on which of the reactants should suitably be used in excess). Obviously, in the synthesis of compounds of formulae (9), (11) and (12) each of the intermediates has a symmetric structure, whereas that of formula (10) is asymmetric.

Amino groups are protected by a group Boc or Z; whereas carboxyl groups are provided with tert-butyl, benzyl or 4-nitrobenzyl ester protecting groups.

After completion of the synthesis, the optionally present protecting groups are removed from the protected peptide obtained in the above manner, and then, if desired, the free peptide is converted to its acid addition salt by treating with an acid. Catalytic hydrogenation or acidolysis are used to remove the protecting groups. The peptides thus obtained are usually sufficiently pure for the therapeutic use and do not require any further purification. However, if desired, they can be purified by column chromatography on silica gel. The peptides obtained in the form of a solution can be isolated by evaporation or lyophilization of the solution. A free peptide can be transformed to an optional salt.

The purity of the final product is checked by using high performance liquid chromatography (HPLC) analysis.

The effect on the immune system of the target compounds was investigated in the tests described hereinafter.

1. Effect on the Antibody-Producing Cells in Newborn Rats

This investigation was carried out with splenocytes obtained from newborn rats according to the method of Canningham (Handbook of Experimental Immunology, Ed. D. M. Weir, Vol. 2., Blackwell, Oxford-London, page 285, 1978). Twelve Wistar (LATI) rats arising from a single litter were intraperitoneally (i.p.) treated with 7.5 μg of test substance in a dose of 1 mg/kg within 12 hours of their birth. On the 14th day after birth, the animals were i.p. immunized by 0.5 ml of an 1% suspension of sheep erythrocytes, then bled by decapitation after 7 days. From the splenocytes obtained from the animals, a homogeneous suspension was prepared using sheep erythrocyte suspension and complement which was then put into a chamber suitable for obtaining a monocellular layer. The chambers closed with paraffin were incubated at 37° C. for 45 minutes. Around the antibody-producing splenocytes, lytic areas, the so-called plaques, were formed. Under the effect of treatment with the suppressing substances, the number of the plaque-forming cells (PFC) was decreased. The data summarized in Table 1 illustrate this percentage decrease calculated on the basis of the cells obtained from the untreated control animals. Under the same conditions, the number of the plaque-forming cells is significantly increased by immunostimulating peptides.

TABLE 1

| Suppression of the antibody production | |
|---|---|
| Peptide | Change % |
| (1) Arg—Lys(Chc)—Asp—Val | −14.4 |
| (2) Arg—Lys(Chc)—Asp | −27.1 |
| (3) Arg—Sar—Asp—Val | −25.5 |
| (4) Arg—Sar—Asp | −21.5 |
| (5) Orn—Lys—Asp—Val | −19.5 |
| (8) Arg—Lys—Aad | −10.6 |

TABLE 1-continued

| Suppression of the antibody production | |
|---|---|
| Peptide | Change % |
| (10) Arg—Lys—Asp—Val—NH—CH₂<br>                                                                      \|<br>     Arg—Lys—Asp—NH—CH₂ | −22.4 |
| (11) (Arg—Lys—Asp—Val—NH—CH₂)₂ | −21.2 |
| (16) Lys—Glu—Thr | −36.8 |
| (17) Lys—Thr—Glu—Thr | −23.2 |
| (18) Pro—Lys—Leu—Thr | −19.4 |
| (19) Lys—Lys—Thr—Glu | −22.9 |
| (20) Lys—His—Leu—NH₂ | −25.3 |
| A Arg—Lys—Asp | +68.6 |
| B Arg—Lys—Asp—Val | +58.0 |
| C Arg—Lys—Asp—Val—Tyr | +46.9 |

2. Effect on the Primary Antibody Production in Newborn Rats

This study is based on the phenomenon of agglutination. A specific antiserum adheres to the surface of the antigen forming large granules which settle rapidly (agglutinate).

Newborn Wistar (LATI) rats were intraperitoneally (i.p.) treated with an 1 mg/kg dose of the test substance within 12 hours after birth. On the 14th day, the animals were i.p. immunized by 0.5 ml of an 1% suspension of sheep erythrocytes. On day 7 following the immunization, blood was taken retroorbitally, after 30 minutes the sera were separated by centrifuging and the haemagglutinin titre was determined according to the method of Takátsy [Acta Microbiol. Acad. Sci. Hung. 3, 191 (1955)]. From the mixed sera (50 μl) of two rats, halving dilutions were prepared in 12 steps. Each sample was given 25 /ul of a 2% suspension of sheep erythroxytes The mixture was incubated at 37° C. for one hour to evaluate the agglutination. The data are summarized in Table 2 which show the suppressing (inhibitory) effect of the compounds on the primary antibody production as a percentage value in relation to the untreated animals. Immunostimulating substances show just the opposite effect in this test.

TABLE 2

| Effect on the primary antibody production | |
|---|---|
| Peptide | Change in relation to the untreated control % |
| (3) Arg—Sar—Asp—Val | −17.9 |
| (4) Arg—Sar—Asp | −10.7 |
| (11) (Arg—Lys—Asp—Val—NH—CH₂)₂ | −14.9 |
| (12) (Arg—Lys—Asp—Cys—NH₂)₂ | −10.7 |
| (19) Lys—Lys—Thr—Glu | −10.8 |
| A Arg—Lys—Asp | +13.7 |
| B Arg—Lys—Asp—Val | +28.1 |
| C Arg—Lys—Asp—Val—Tyr | +41.3 |

3. Inhibition of the Phagocytating Capacity of Resting Macrophages

The phagocytating capacity of resting macrophage cells was investigated on mice [J. Immunopharmacol. 4, 265 (1982-1983)]. Male CFLP (LATI) mice weighing 22 to 28 g were subcutaneously (s.c.) treated daily with a 1 mg/kg dose of the test substance for 7 days. After bleeding the animals, their peritonea were washed with 8 ml of PBS buffer solution (phosphate buffered saline, pH=7.2) each containing 10 IU of heparin. The cell suspension washed out from the peritoneum was made free of the erythrocytes by shocking with distilled water, then washed 3 times with PBS buffer solution. The sedimentation between two washings was achieved by centrifuging at 1000 rpm for 5 minutes. The concentration of each cell suspension was adjusted to $10^6$ cell/ml and the suspension was settled for 30 minutes in a Boyden-chamber at 37° C. in an atmosphere containing 5% of carbon dioxide. Over the macrophages adhered to the glass wall, opsonized yeast was layered. After removing the non-phagocytated particles, those incorporated by the macrophages were counted in each cell. In Table 3, the percentage of decrease in the count of phagocytated yeast cells is given in relation to the macrophages isolated from the untreated animals as control.

TABLE 3

| Change in the phagocytating capacity of resting macrophages | |
|---|---|
| Peptide | Change % |
| (1) Arg—Lys(Chc)—Asp—Val | −11.2 |
| (2) Arg—Lys(Chc)—Asp | −47.3 |
| (3) Arg—Sar—Asp—Val | −10.5 |
| (4) Arg—Sar—Asp | −22.7 |
| (7) Arg—Lys—Aad—Val | −28.7 |
| (8) Arg—Lys—Aad | −29.1 |
| (9) (Arg—Lys—Asp—NH—CH₂)₂ | −11.6 |
| (11) (Arg—Lys—Asp—Val—NH—CH₂)₂ | −16.5 |
| (12) (Arg—Lys—Asp—Cys—NH₂)₂ | −40.1 |
| (14) Ser—Lys—Leu | −14.0 |
| (17) Lys—Thr—Glu—Thr | −17.5 |
| (18) Pro—Lys—Leu—Thr | −11.7 |
| (19) Lys—Lys—Thr—Glu | −18.6 |
| (20) Lys—His—Leu—NH₂ | −39.6 |
| Cyclophosphamide in a 150 mg/kg i.p. dose | −75.0 |

4. Effect on the Late Hypersensitive (DTH) Response

This test was carried out on male CFLP (LATI) mice weighing 25 to 30 g. At the beginning of the experiment, the mice were treated with a 3% solution of oxazolone in anhydrous ethanol by applying 20 μl of solution each on both ears and forepaws. On day 7 following the treatment, the animals were treated with a 1 mg/kg i.p. dose of the compounds dissolved in physiological saline solution. The controls were treated only with saline. On day 10 of the experiment, 20 μl of an 2.5% olive oil solution of oxazolone were smeared on each ear of the animals. The thickness of the ears was twice measured, i.e. before and 24 hours after the administration of the antigen. The thickness was measured on both ears in the middle of the ear-lobes with an accuracy of 0.01 mm. The change was compared with the control group. The data concerning the suppression of the development of a DTH response are given as percentage values in Table 4.

TABLE 4

| Suppression of the DTH response | |
|---|---|
| Peptide | Suppression % |
| (1) Arg—Lys(Chc)—Asp—Val | 39.1 |
| (5) Orn—Lys—Asp—Val | 28.3 |
| (6) Orn—Lys—Asp | 39.6 |
| (8) Arg—Lys—Aad | 36.8 |
| (11) (Arg—Lys—Asp—Val—NH—CH₂)₂ | 27.0 |

TABLE 4-continued

Suppression of the DTH response

| Peptide | Suppression % |
|---|---|
| (12) (Arg—Lys—Asp—Cys—NH$_2$)$_2$ | 35.3 |
| (13) Lys—Ser—Lys—Leu | 28.2 |
| (14) Ser—Lys—Leu | 22.7 |
| (15) Ser—Ser—Ser—Thr | 18.0 |
| (16) Lys—Glu—Thr | 27.5 |
| (17) Lys—Thr—Glu—Thr | 35.5 |
| Cyclophosphamide in a 150 mg/kg i.p. dose | 72 |

The peptides "A", "B" and "C" given in the above Tables for comparison are known:

"A" and "B" are described in the Hungarian patent specification No. 185,263;

"C" is known from the U.S. Pat. No. 4,190,646.

The compounds of the invention and their acid addition salts can be used in the form of common pharmaceutical compositions in any therapeutic area where a decrease in the activity of the immune system is desired. The peptides of formulae (1) to (20) are used per se or in the form of their salts, suitably in a pharmaceutical formulation commonly used in therapy. These formulations (medicaments) may be in a solid or liquid state and can be prepared by using fillers, diluents, stabilizers pH- and osmotic pressure-influencing agents as well as addivites promoting the formulation commonly used in such formulations.

The invention is illustrated in detail by the following non-limiting Examples.

The abbreviations used in the description correspond to those generally known in the literature [Biochem. J. 219, 345 (1984)]. "Chc" means cyclohexylcarbamoyl and "Aad" is α-L-aminoadipoyl group. The melting points were determined in a Dr. Tottoli device (manufactured by Büchi, Switzerland). Thin layer chromatography examinations were carried out by using a ready-for-use adsorbent (DC-Fertigplatten, manufactured by Merck, FRG) and the following solvent mixtures (where the "stock solution" is a 20:6:11 mixture of pyridine/acetic acid/water):

| 1. ethyl acetate/stock solution | 19:1; |
| 2. ethyl acetate/stock solution | 9:1; |
| 3. ethyl acetate/stock solution | 4:1; |
| 4. ethyl acetate/stock solution | 7:3; |
| 5. n-butanol/stock solution | 3:7; |
| 6. n-butanol/stock solution | 1:4; and |
| 7. n-butanol/acetic acid/ethyl acetate/water | 1:1:1:1. |

(The ratios are given in volume-ratio values.)

The chromatograms were detected by ninhydrin or, after chlorination, by using the potassium iodide/tolidine reagent.

The HPLC analyses were carried out by using a device equipped with a Labor-MIM OE 975 type UV detector with variable wave-length, Altex pump and KUTESZ 175 type recorded. For the separation, a charge of 250 mm in length, 4.6 mm in inner diameter, with a resting phase of silica gel alkylated by C$_{18}$alkyl groups (Labor MIM) was used. The following mixtures were employed for elution:

A. A mixture consisting of 25 ml of methanol and 75 ml of 0.01M aqueous sodium sulphate containing 0.5% by volume of trifluoro-acetic acid;

B. A 1.5:1.0:97.5 mixture of acetonitrile/trifluoroacetic acid/distilled water.

The measurement was accomplished at a flow rate of 1 ml/min and the absorption of the solution was detected at 212 nm. The chromatograms were evaluated by area-normalization.

The purity of the target compounds was higher than 95% based on both HPLC and thin layer chromatography (TLC) analyses.

The specific optical rotation was determined in a Perkin-Elmer 241 type polarimeter. All solvents were removed or evaporated in a Büchi rotating evaporator in a water bath at 40° C.

The amino acid analyses of the target compounds was carried out in a Biotronik LC 5001 type equipment. The samples were hydrolyzed in a hydrochloric acid solution of 6 molar concentration at 110° C. for 24 hours. The results of the analyses were in all cases within an error limit of ±5%.

The starting substances of the syntheses are commonly known in the literature.

EXAMPLE 1

Preparation of Arg-Sar-Asp-Val (method "A")

1.68 ml (12.0 mmol) of triethylamine are added to a suspension containing 2.58 g (12.0 mmol) of H-Val-O$^t$Bu.HCl and 4.62 g (11.0 mmol) of Z-Asp(O$^t$Bu)-OSu in 25 ml of dimethylformamide (DMF). The reaction mixture is left to stand overnight, then evaporated under reduced pressure. The residue is mixed with 50 ml of ethyl acetate and the suspension obtained is successively washed with 25 ml of water, 3 times with 25 ml of 1 mol/liter hydrochloric acid each, 3 times with 25 ml of 5% aqueous sodium hydrogenocarbonate each and finally with 25 ml of water, dried over anhydrous sodium sulfate and evaporated under reduced pressure to obtain 4.3 g (81.7%) of oily Z-Asp(O$^t$Bu)-Val-O$^t$Bu protected dipeptide, $R_f^1 = 0.85$.

4.07 g (8.5 mmol) of the above protected dipeptide are dissolved in 40 ml of methanol and hydrogenated by bubbling hydrogen through the solution in the presence of 1.0 g of palladium-on-carbon while stirring. The hydrogenation is completed within 2 hours. Then, the catalyst is filtered off, the filtrate is evaporated under reduced pressure, the residue is dissolved in 50 ml of ether and the pH is adjusted to 4 by adding dioxanic hydrogen chloride solution of 6 mol/liter concentration. The precipitate is filtered off to give 3.2 g (91.5%) of H-Asp(O$^t$Bu)-Val-O$^t$Bu.HCl free dipeptide hydrochloride, m.p.: 187°–189° C., $R_f^2 = 0.40$.

3.0 g (10.0 mmol) of Z-Sar-OSu and 3.05 g (8.0 mmol) of H-Asp(O$^t$Bu)-Val-O$^t$Bu.HCl in 30 ml of DMF are reacted in the presence of 1.40 ml (10.0 mmol) of triethylamine. The next day the reaction mixture is evaporated under reduced pressure, the residue is dissolved in 50 ml of ethyl acetate and the suspension obtained is successively washed with 20 ml of water, twice with 20 ml of 1 mol/liter hydrochloric acid each, twice with 20 ml of 5% sodium hydrogenocarbonate solution each and finally with 20 ml of water, dried over anhydrous sodium sulfate and evaporated under reduced pressure.

The oily Z-Sar-Asp(O$^t$Bu)-Val-O$^t$Bu protected tripeptide obtained in a yield of 4.2 g (7.6 mmol) ($R_f^1 = 0.75$) is dissolved in 40 ml of methanol and, after adding 0.8 g of palladium-on-carbon catalyst, the mixture is hydrogenated in the usual manner. After filtering off the catalyst, 1.0 g (8.0 mmol) of oxalic acid dihydrate is added to the filtrate, the solution is evaporated and the residue is solidified by adding ether to obtain 2.24 g of H-Sar-Asp(O$^t$Bu)-Val-O$^t$Bu.oxalate (free tripeptide oxalate), m.p.: 190°–192° C., $R_f^3$=0.30.

A solution of 1.14 g (3.5 mmol) of Boc-Arg(HCl)-OH.H$_2$O in 10 ml of DMF is cooled to −10° C., 0.55 ml (4 mmol) of isobutyl chloroformate then a solution of 0.44 ml (4 mmol) of N-methylmorpholine dissolved in 5 ml of DMF are added at the same temperature. The mixed anhydride obtained is stirred at −10° C. for 10 minutes, then a solution of 1.5 g (3 mmol) of the free tripeptide oxalate obtained above and 0.84 ml (6 mmol) of triethylamine in 5 ml of DMF are added at the same temperature. The reaction mixture is allowed to warm to room temperature and left to stand overnight. The solvent is evaporated under reduced pressure, the residue is dissolved in 50 ml of chloroform and this solution is washed 3 times with 20 ml of 1 mol/liter hydrochloric acid each, then with 20 ml of water and dried over anhydrous sodium sulfate. The oily residue is solidified by adding ether and the suspension is filtered to give 1.30 g (66%) of amorphous Boc-Arg(HCl)-Sar-Asp(O$^t$-Bu)-Val-O$^t$Bu, $R_f^3$=0.18, $R_f^4$=0.24; $/\alpha/_D^{20}$= −37.0° (c=1, methanol).

1.20 g (1.8 mmol) of the protected tetrapeptide obtained above are treated with trifluoroacetic acid at 40° C. for 2 hours, then the mixture is diluted by adding 60 ml of ether, the suspension is filtered and the precipitate is washed with ether. After dissolving the trifluoroacetate salt in 10 ml of water, the trifluoroacetate ions are replaced by acetate ions by the means of 5 ml of anion-exchange resin of acetate cycle (DOWEX 2×8). After evaporating the solution under reduced pressure, the residue is solidified by adding 5 ml of 90% aqueous ethanol to obtain 0.6 g of amorphous Arg-Sar-Asp-Val; $/\alpha/_D^{20}$= −32.3° (c=1, 10% acetic acid). Amino acid analysis: Asp 1.03 (1), Val 0.97 (1), Arg 1.00 (1).

EXAMPLE 2

Preparation of Lys-Glu-Thr (method "B")

After suspending 3.3 g (11.0 mmol) of H-Thr($^t$Bu)-O$^t$Bu.oxalate in 60 ml of ether, the suspension is shaken with 30 ml of 5% aqueous potassium hydrogenocarbonate solution until dissolving. The organic phase is separated, washed with an additional 20 ml of 5% aqueous potassium hydrogenocarbonate solution and then with 20 ml of water, dried over anhydrous sodium sulfate and evaporated under reduced pressure. To the solution of the oily residue in 20 ml of DMF, 4.12 g (9.5 mmol) of Z-Glu(O$^t$Bu)-OSu are added. The mixture is stirred at room temperature for 2 hours then evaporated under reduced pressure. The residue is dissolved in 50 ml of ethyl acetate and successively washed three times, three times with 15 ml of 10% aqueous citric acid solution each, twice with 15 ml of 5% aqueous sodium hydrogenocarbonate solution each, and finally with 15 ml of water, dried over anhydrous sodium sulfate and evaporated under reduced pressure. 4.4 g (8.0 mmol) of oily Z-Glu(O$^t$Bu)-Thr($^t$Bu)-O$^t$Bu protected dipeptide ($R_f^1$=0.85) are obtained which is dissolved in 50 ml of methanol and hydrogenated as described in Example 1. After filtering off the catalyst, the filtrate is evaporated to yield the free H-Glu(O$^t$-Bu)-Thr($^t$Bu)-O$^t$Bu dipeptide ($R_f^2$=0.22) which is then dissolved in 20 ml of DMF and after adding 4.77 g (10 mmol) of Z-Lys(Boc)-OSu, the reaction mixture is stirred at room temperature for 2 hours and evaporated under reduced pressure. After dissolving the oily residue in 50 ml of ethyl acetate, the solution is purified by several washings in the usual manner, dried over anhydrous sodium sulfate and evaporated under reduced pressure. The oily evaporation residue is recrystallized in ether to yield 4.75 g (74%) of Z-Lys(Boc)-Glu(O$^t$Bu)-Thr($^t$Bu)-O$^t$Bu protected tripeptide, m.p.: 114°–115° C.; $R_f^2$=0.80; $/\alpha/_D^{20}$= −22.8° (c=1, methanol).

4.4 g (5.6 mmol) of the above protected tripeptide are dissolved in 40 ml of methanol and catalytically hydrogenated as described in Example 1. After filtering off the catalyst, the filtrate is evaporated under reduced pressure and the oily residue is dissolved in 40 ml of dioxanic hydrogen chloride solution of 6 mol/liter concentration. After 15 minutes a precipitate appears. After one hour, the suspension is diluted with 100 ml of ether, filtered and the precipitate is washed with ether to give 2.3 g (91%) of amorphous Lys-Glu-Thr.2HCl tripeptide dihydrochloride, m.p.: 213°–215° C. (with decomposition); $/\alpha/_D^{20}$= +2.7° (c=1, 1.1% acetic acid).

After dissolving the above Lys-Glu-Thr.2HCl tripeptide dihydrochloride in 20 ml of water, the chloride ions are replaced by acetate ions on a resin of acetate cycle (DONEX 2×8), then the solution is evaporated under reduced pressure and the residue is solidified by adding ethanol. In this way 2.27 g of amorphous Lys-Glu-Thr-acetate are obtained; $/\alpha/_D^{20}$= +3.5° (c=1, 10% acetic acid). Amino acid analysis: Glu 1.01 (1), Thr 1.00 (1), Lys 1.00 (1).

EXAMPLE 3

Preparation of Lys-His-Leu-NH$_2$acetate (method "C")

To a solution of 2.42 g (10 mmol) of His.OMe.2HCl in 30 ml of DMF, 2.8 ml (20 mmol) of triethylamine and then 5.6 g (11 mol) of Z-Lys(Z)-OSu are added. Next day the reaction mixture is evaporated, the oily residue is dissolved in 45 ml of chloroform, the solution is washed twice with 20 ml of water each, dried over anhydrous sodium sulfate and evaporated under reduced pressure. After solidifying the oily residue by adding ethyl acetate, 4.54 g (80%) of Z-Lys(Z)-His-OMe are obtained, m.p.: 135°–136° C., $R_f^3$=0.45.

4.0 g (7 mmol) of the protected dipeptide ester obtained above are dissolved in 40 ml of warm methanol and 4 ml of hydrazine hydrate are added. The mixture is kept at room temperature for 3 days, then evaporated to its half volume under reduced pressure and diluted with 50 ml of ether. The amorphous precipitate is filtered and washed with ether to give 3.70 g of Z-Lys(H)-His-N$_2$H$_3$ protected dipeptide hydrazide, m.p.: 150°–153° C.; $R_f^3$=0.20.

A solution containing 3.65 g (6.0 mmol) of the above Z-Lys(Z)-His-N$_2$H$_3$ in 15 ml of DMF is cooled to −10° C. and 2.5 ml of dioxanic hydrogen chloride of 7 mol/liter concentration and then 0.75 ml (6.6 mmol) of tertiary butyl nitrite in 4 ml of DMF are dropwise added at the same temperature. After stirring the reaction mixture at −10° C. for 20 minutes, 2.0 ml of triethylamine are added and then, a solution of 1.33 g (7 mmol) of Leu-NH$_2$ acetate and 1 ml of triethylamine in 10 ml of DMF are dropped. The mixture is then stirred at 0° C. for 30 minutes, then left at room temperature overnight. The reaction mixture is evaporated under reduced pressure and the residue is suspended in water. 3.7 g of crude product are obtained which is recrystallized from 30 ml of isopropanol to obtain 2 g (65%) of Z-Lys(Z)-His-Leu-NH$_2$, m.p.: 110°–113° C., $R_f^4$=0.30; $/\alpha/_D^{20}$= −20.1° (c=1, methanol).

1.2 g (1.8 mmol) of protected tripeptide obtained above are dissolved in 20 ml of a 5:1:2 mixture of methanol/water/acetic acid and catalytically hydrogenated as described in Example 1. After filtering off the catalyst, the filtrate is evaporated under reduced pressure. After adding ethanol to the residue and evaporating, the residue is triturated with ether to give 0.57 g of amorphous hygroscopic Lys-His-Leu-NH$_2$-acetate; /α/$_D^{20}$= −5.7° (c=1, in 1 mol/liter acetic acid).

Amino acid analysis: Leu 0.95 (1), His 1.03 (1), Lys 1.04 (1).

The protected peptide derivatives shown in Table 5 and the target compounds indicated in Table 6 were prepared by following the processes described in the Examples in detail.

TABLE 5

Protected peptides prepared according to the above preparation Examples, method of preparation and physical characteristics

| | Protected peptide | Method | /α/$_D^{20}$ | R$_f$ (mixture) |
|---|---|---|---|---|
| 1 | Boc—Arg(HCl)—Lys(Chc)—Asp(O$^t$Bu)—Val—O$^t$Bu | A | −30.8° | 0.28 (4) |
| 2 | Boc—Arg(HCl)—Lys(Chc)—Asp(O$^t$Bu)—O$^t$Bu | A | −20.6° | 0.45 (4) |
| 3 | Boc—Arg(HCl)—Sar—Asp(O$^t$Bu)—Val—O$^t$Bu | A | −37.0° | 0.24 (4) |
| 4 | Boc—Arg(HCl)—Sar—Asp(O$^t$Bu)—O$^t$Bu | A | −20.4° | 0.25 (4) |
| 5 | Boc—Orn(Boc)—Lys(Boc)—Asp(O$^t$Bu)—Val—O$^t$Bu | A | −31.6° | 0.76 (2) |
| 6 | Boc—Orn(Boc)—Lys(Boc)—Asp(O$^t$Bu)—O$^t$Bu | A | −21.3° | 0.76 (2) |
| 7 | Boc—Arg(HCl)—Lys(Boc)—Aad(O$^t$Bu)—Val—O$^t$Bu | A | −32.6° | 0.40 (4) |
| 8 | Boc—Arg(Hcl)—Lys(Boc)—Aad(O$^t$Bu)—O$^t$Bu | A | −21.2° | 0.40 (4) |
| 9 | [Boc—Arg(HCl)—Lys(Boc)—Asp(O$^t$Bu)—NH—CH$_2$]$_2$ | A | −80.8° | 0.25 (4) |
| 10 | Boc—Arg(HCl)—Lys(Boc)—Asp(O$^t$Bu)—Val—NH—CH$_2$ \| Boc—Arg(HCl)—Lys(Boc)—Asp(O$^t$Bu)—NH—CH$_2$ | A | −29.6° | 0.35 (4) |
| 11 | [Boc—Arg(HCl)—Lys(Boc)—Asp(O$^t$Bu)—Val—NH—CH$_2$]$_2$ | A | −39.0° | 0.35 (4) |
| 12 | [Boc—Arg(HCl)—Lys(Boc)—Asp(O$^t$Bu)—Cys—NH$_2$]$_2$ | A | −61.0° | 0.50 (4) |
| 13 | Z—Lys(Boc)—Ser($^t$Bu)—Lys(Boc)—Leu—O$^t$Bu | B | −29.9° | 0.70 (2) |
| 14 | Z—Ser($^t$Bu)—Lys(Boc)—Leu—O$^t$Bu | B | −28.6° | 0.80 (2) |
| 15 | Z—Ser($^t$Bu)—Ser($^t$Bu)—Ser($^t$Bu)—Thr($^t$Bu)—O$^t$Bu | B | | 0.80 (1) |
| 16 | Z—Lys(Boc)—Glu(O$^t$Bu)—Thr($^t$Bu)—O$^t$Bu | B | −22.8° | 0.80 (2) |
| 17 | Z—Lys(Boc)—Thr($^t$Bu)—Glu(O$^t$Bu)—Thr($^t$Bu)—O$^t$Bu | B | | 0.85 (2) |
| 18 | Boc—Pro—Lys(Boc)—Leu—Thr($^t$Bu)—O$^t$Bu | B | −58.7° | 0.75 (2) |
| 19 | Boc—Lys(Boc)—Lys(Boc—Thr($^t$Bu)—Glu(O$^t$Bu)—O$^t$Bu | B | −15.1° | 0.77 (2) |
| 20 | Z—Lys(Z)—His—Leu—NH$_2$ | C | −20.1° | 0.30 (4) |

TABLE 6

Further target compounds prepared according to the above preparation Examples and their physical characteristics

| Target compound | /α/$_D^{20}$ in 10% acetic acid | /α/$_D^{20}$ in 1 mol/liter acetic acid | /α/$_D^{20}$ in 100% | R$_f$ (mixture) (5) | (6) | (7) | (stock soln.) |
|---|---|---|---|---|---|---|---|
| (1) Arg—Lys(Chc)—Asp—Val | −17.8° | | | 0.50 | | | |
| (2) Arg—Lys(Chc)—Asp | +1.0° | | | 0.50 | | | |
| (3) Arg—Sar—Asp—Val | −32.3° | −21.8° | | 0.26 | 0.18 | | |
| (4) Arg—Sar—Asp | +11.3° | +9.0° | | 0.24 | 0.14 | | |
| (5) Orn—Lys—Asp—Val | −25.9° | | | 0.10 | 0.13 | | |
| (6) Orn—Lys—Asp | −1.5° | | | 0.05 | 0.12 | | |
| (7) Arg—Lys—Aad—Val | −24.4° | | | 0.15 | | | |
| (8) Arg—Lys—Aad | −2.6° | | | 0.07 | | | |
| (9) [Arg—Lys—Asp—NH—CH$_2$]$_2$ | −18.7° | | | | | | 0.15 |
| (10) Arg—Lys—Asp—Val—NH—CH$_2$ \| Arg—Lys—Asp—NH—CH$_2$ | 0° | −57.2° | | | | | 0.10 |
| (11) [Arg—Lys—Asp—Val—NH—CH$_2$]$_2$ | −35.5° | | | 0.05 | | | |
| (12) [Arg—Lys—Asp—Cys—NH$_2$]$_2$ | −72.8° | | | 0.03 | | | |
| (13) Lys—Ser—Lys—Leu | −27.8° | | | 0.19 | 0.19 | | |
| (14) Ser—Lys—Leu | −30.0° | | | 0.54 | 0.34 | | |
| (15) Ser—Ser—Ser—Thr | −32.4° | | | 0.24 | 0.37 | | |
| (16) Lys—Glu—Thr | +3.5° | | | 0.16 | 0.15 | | |
| (17) Lys—Thr—Glu—Thr | −25.0° | | | 0.20 | 0.10 | | |
| (18) Pro—Lys—Leu—Thr | | −57.7° | | 0.34 | 0.17 | | |
| (19) Lys—Lys—Thr—Glu | | −21.7° | | 0.12 | 0.10 | | |
| (20) Lys—His—Leu—NH$_2$ | | −5.7° | | 0.34 | 0.10 | | |

What is claimed is:

1. A compound of the formula (1) to (20)

| | |
|---|---|
| Arg-Lys(Chc)-Asp-Val | (1) |
| Arg-Lys(Chc)-Asp | (2) |
| Arg-Sar-Asp-Val | (3) |
| Arg-Sar-Asp | (4) |
| Orn-Lys-Asp-Val | (5) |
| Orn-Lys-Asp | (6) |
| Arg-Lys-Aad-Val | (7) |
| Arg-Lys-Aad | (8) |
| [Arg-Lys-Asp-NH-CH$_2$-]$_2$ | (9) |
| Arg—Lys—Asp—Val—NH—CH$_2$<br>                                                                \|<br>Arg—Lys—Asp—NH—CH$_2$ | (10) |
| [Arg—Lys—Asp—Val—NH—CH$_2$—]$_2$ | (11) |
| [Arg—Lys—Asp—Cys—NH$_2$]$_2$ | (12) |
| Lys-Ser-Lys-Leu | (13) |
| Ser-Lys-Leu | (14) |
| Ser-Ser-Ser-Thr | (15) |
| Lys-Glu-Thr | (16) |
| Lys-Thr-Glu-Thr | (17) |
| Pro-Lys-Leu-Thr | (18) |
| Lys-Lys-Thr-Glu | (19) or |
| Lys-His-Leu-NH$_2$ | (20) | or a pharmaceutically acceptable acid addition salt thereof.

2. (amended)

{Arg—Lys—Asp—Cys—NH$_2$}$_2$ or a pharmaceutically acceptable acid addition salt thereof.

3. A compound selected from the group consisting of:

Arg-Sar-Asp-Val

Arg-Sar-Asp

Orn-Lys-Asp-Val

Orn-Lys-Asp

Arg-Lys-Aad-Val

Arg-Lys-Aad

[Arg-Lys-Asp-NH-CH$_2$-]$_2$

Arg—Lys—Asp—Val—NH—CH$_2$
                                         |
Arg—Lys—Asp—NH—CH$_2$

[Arg—Lys—Asp—Val—NH—CH$_2$—]$_2$

[Arg—Lys—Asp—Cys—NH$_2$]$_2$

Lys-Ser-Lys-Leu

Ser-Lys-Leu

Ser-Ser-Ser-Thr

Lys-Glu-Thr

Lys-Thr-Glu-Thr

Pro-Lys-Leu-Thr

Lys-Lys-Thr-Glu and

Lys-His-Leu-NH$_2$ or a pharmaceutically acceptable acid addition salt thereof.

4. (twice amended) A pharmaceutical composition, which comprises as active ingredient a compound of the formulae (1) to (20) in free form or in the form of an acid addition salt as defined in claim 1 in a therapeutically effective amount in admixture with a pharmaceutically acceptable inert carrier.

* * * * *